United States Patent
Anthony et al.

(10) Patent No.: US 8,529,445 B2
(45) Date of Patent: Sep. 10, 2013

(54) SPREADING RETRACTOR

(75) Inventors: Sarah M. Anthony, Leesburg, IN (US);
Kyle E. Lappin, Fort Wayne, IN (US);
Joseph P. Iannotti, Strongsville, OH (US); Gerald R. Williams, Villanova, PA (US); Michael A. Wirth, San Antonio, TX (US)

(73) Assignee: Depuy Synthes Products, LLC, Raynham, MA (US)

( * ) Notice: Subject to any disclaimer, the term of this patent is extended or adjusted under 35 U.S.C. 154(b) by 166 days.

(21) Appl. No.: 12/938,800

(22) Filed: Nov. 3, 2010

(65) Prior Publication Data

US 2011/0282158 A1  Nov. 17, 2011

Related U.S. Application Data

(60) Provisional application No. 61/345,328, filed on May 17, 2010.

(51) Int. Cl.
*A61B 1/32* (2006.01)

(52) U.S. Cl.
USPC .......................................... 600/215; 600/235

(58) Field of Classification Search
USPC ................... 606/90; 600/201, 213, 215, 216, 600/219, 235, 240; 81/302, 418, 420, 421, 81/424, 426.5
See application file for complete search history.

(56) References Cited

U.S. PATENT DOCUMENTS

| | | | |
|---|---|---|---|
| 5,030,219 A | 7/1991 | Matsen, III | |
| 5,437,677 A | 8/1995 | Shearer | |
| 6,042,540 A * | 3/2000 | Johnston et al. | 600/213 |
| 6,277,136 B1 | 8/2001 | Bonutti | |
| 7,264,589 B2 | 9/2007 | Sharratt | |
| 7,294,133 B2 | 11/2007 | Zink | |
| 2004/0199252 A1 | 10/2004 | Sears | |
| 2007/0239157 A1 | 10/2007 | Guillaume | |
| 2009/0137984 A1* | 5/2009 | Minnelli | 604/540 |

FOREIGN PATENT DOCUMENTS

| | | |
|---|---|---|
| EP | 1905395 A1 | 4/2008 |
| EP | 1905395 B1 | 8/2009 |
| WO | WO 03099146 A2 | 12/2003 |
| WO | WO 03099146 A3 | 3/2005 |
| WO | WO 2006093763 A2 | 9/2006 |
| WO | WO 2006093763 A8 | 11/2007 |
| WO | WO 2006093763 A3 | 4/2009 |
| WO | WO 2010017307 A1 * | 2/2010 |
| WO | WO 2010053994 A1 | 5/2010 |

* cited by examiner

*Primary Examiner* — Kevin T Truong
*Assistant Examiner* — Christian Sevilla (57) ABSTRACT

A spreadable retractor for use in joint arthroplasty. The retractor includes a first arm having a first portion and a second portion that is movably coupled to the first portion. The second portion is also coupled to a first retaining member that is sized and shaped to retain a portion of a coracoid process. A second arm is also included in the retractor and is movably coupled to the first arm. The second arm has a first portion and a second portion that is movably coupled to the first portion. Also, the second portion is coupled to a second retaining member that is sized and shaped to couple to a resected humerus.

5 Claims, 6 Drawing Sheets

SPREADING RETRACTOR

CROSS-REFERENCE TO RELATED APPLICATION

Priority is claimed to the following application: U.S. Provisional Patent Application Ser. No. 61/345,328 entitled, "SPREADING RETRACTOR," filed on May 17, 2010 by Sarah Anthony, Kyle Lappin, Joseph Iannotti and Gerald Williams.

TECHNICAL FIELD

The present invention relates generally to an instrument for use in orthopaedic surgery, and more particularly to an instrument for spreading and retracting muscles, bone, and/or soft tissue during orthopaedic surgery.

BACKGROUND OF THE INVENTION

During the lifetime of a patient, it may be necessary to perform a total shoulder replacement procedure on the patient as a result of, for example, disease or trauma. In a total shoulder replacement procedure, a humeral component having a head portion is utilized to replace the natural head portion of the arm bone or humerus. The humeral component typically has an elongated intramedullary stem which is utilized to secure the humeral component to the patient's humerus. In such a total shoulder replacement procedure, the natural glenoid surface of the scapula is resurfaced or otherwise replaced with a glenoid component which provides a bearing surface for the head portion of the humeral component.

During surgery, first the humeral head is prepared as is known in the art. Then, the surgeon moves to prepare the glenoid. First, it is useful to inspect the posterior aspect of the capsule and glenohumeral space. The surgeon then releases the posterior capsule from the glenoid rim. This step allows for complete removal of the anterior inferior capsule. Any osteophytes are removed and the tissue is then placed back into physiologic tension. The surgeon then needs access to achieve final exposure to the glenoid. However, gaining access to the glenoid during a total shoulder replacement procedure is challenging. Various "shoe-horn" type retractors have been used to gain access to the glenoid. However, these types of retractors need to be held in place by people during the surgery, so they increase the number of people who are required to be involved in the surgical procedure. Also, because of the shape, the retractors may actually limit exposure to the wound site, giving the surgeon less access than may be needed or desired.

Therefore, there is a need for an improved retractor that can expose the glenoid with limited number of people having to hold it.

SUMMARY OF THE INVENTION

According to one embodiment of the present invention, a spreadable retractor for use in joint arthroplasty includes a first arm having a first portion and a second portion. The second portion is movably coupled to the first portion. Also, the second portion is coupled to a first retaining member and the retaining member sized and shaped to retain a portion of a coracoid process. The retractor also includes a second arm movably coupled to the first arm. The second arm having a first portion and a second portion that is movably coupled to the first portion. The second portion is coupled to a second retaining member that is sized and shaped to couple to a resected humerus.

According to another embodiment, a spreadable retractor for use in joint arthroplasty includes a first arm having a first portion and a second portion that is coupled to the first portion. The second portion is also coupled to a first retaining member that is sized and shaped to retain a portion of a coracoid process. The retractor also includes a second arm movably coupled to the first arm. The second arm has a first portion and a second portion that is coupled to the first portion. Also, the second portion is coupled to a second retaining member that is sized and shaped to abut a resected humerus.

According to yet another embodiment of the present invention, a method for retraction useable in joint arthroplasty includes using a joint retractor having a first arm and a second arm. The first arm has a first portion and a second portion and the second arm having a first portion and a second portion. The retractor is inserted into a surgical opening of a patient's shoulder joint. The second portion of the first arm is placed against the coracoid process. The second portion of the second arm is placed against the resected humerus. The first portions of the first and second arms are hung over the resected tissue to allow exposure of the glenoid.

BRIEF DESCRIPTION OF THE DRAWINGS

For a more complete understanding of the present invention and the advantages thereof, reference is now made to the following description taken in connection with the accompanying drawings, in which.

DETAILED DESCRIPTION OF THE DRAWINGS

Embodiments of the present invention and the advantages thereof are best understood by referring to the following descriptions and drawings, wherein like numerals are used for like and corresponding parts of the drawings.

Figure 1:
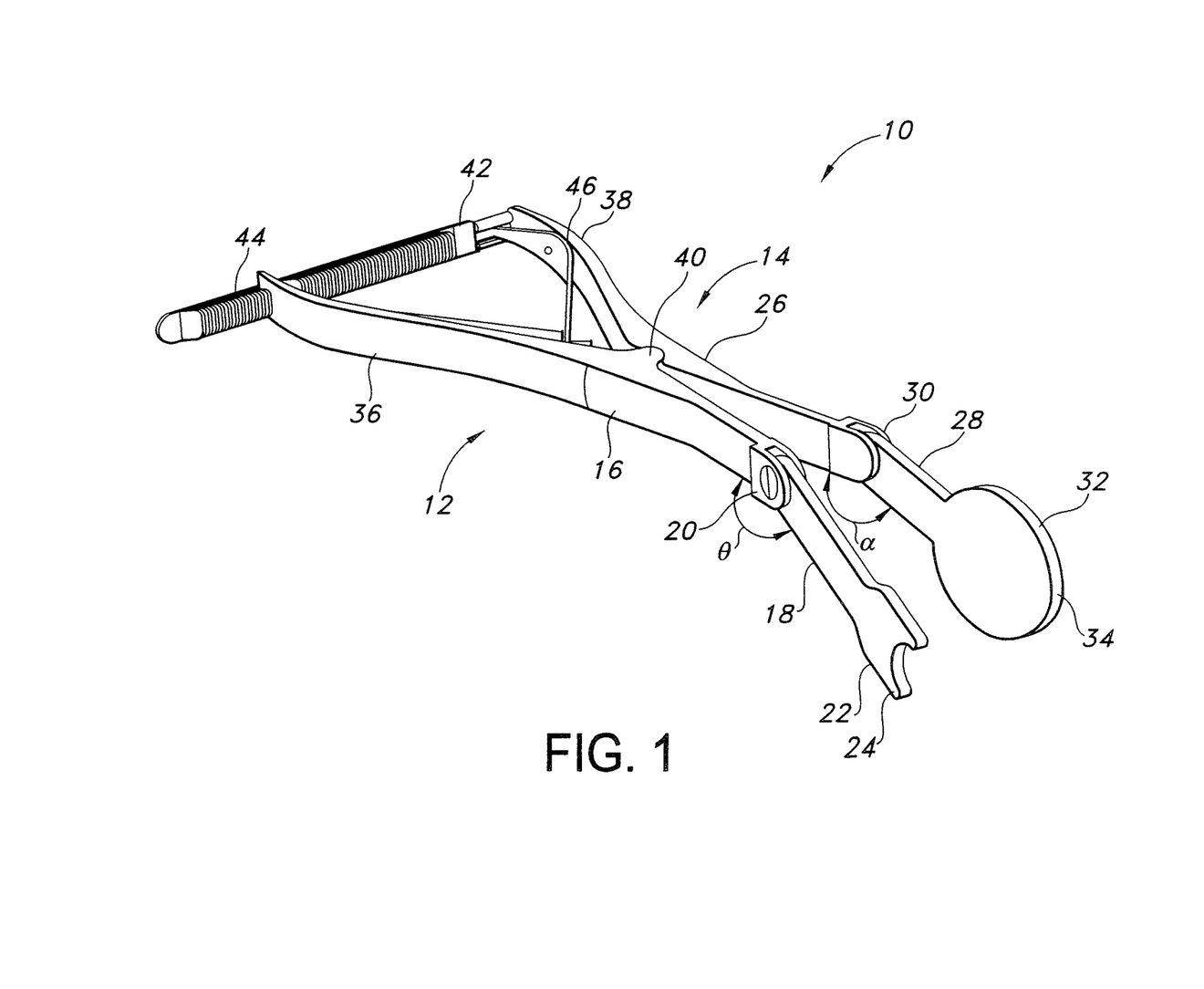
FIG. 1 is a perspective view of a retractor according to one embodiment of the present invention.

Turning now to a FIG. 1, a spreadable retractor 10 for use in joint arthroplasty according to one embodiment of the present invention is illustrated. The retractor 10 includes a first arm 12 and a second arm 14. The first arm 12 has a first portion 16 and a second portion 18. The first portion 16 is movably coupled to the second portion 18. In this embodiment, the first portion 16 and the second portion 18 are coupled via a hinge 20. However, in other embodiments, other coupling mechanisms that allow the second portion 18 to move relative to the first portion 16 may be used. The hinge 20 allows the second portion 18 to be set at an angle θ relative to the first portion 16.

The second portion 18 is coupled to a first retaining member 22. The retaining member 22 is sized and shaped to retain a portion of a coracoid process (shown in FIG. 2). In the illustrated embodiment, the retaining member 22 is a u-shaped member 24 that is designed to press against the coracoid process. Also, in the illustrated embodiment, the retaining member 22 and the second portion 18 are integral with one another. However, in other embodiments, the retaining member 22 may be a separate part from the second portion 18. In such embodiments, the retaining member 22 may be fixedly coupled to the second portion 18 or the retaining member 22 may be movably coupled to the second portion 18. In some embodiments, the retaining member 22 may be pivotally coupled to the second portion 18. In the embodiment where the first retaining member is not integral with the second portion 18, any known connection method may be used (whether fixedly connecting or movably connecting).

The second arm 14 of the spreadable retractor 10 is movably coupled to the first arm 12. The second arm 14 includes a first portion 26 and a second portion 28 that is movably coupled to the first portion 26. In the illustrated embodiment, the first portion 26 is coupled to the second portion 28 via a hinge 30. However, in other embodiments, other coupling mechanisms that allow the second portion 28 to move relative to the first portion 26 may be used. The hinge 30 allows the second portion 28 to be set at an angle α relative to the first portion 26.

Figure 2:
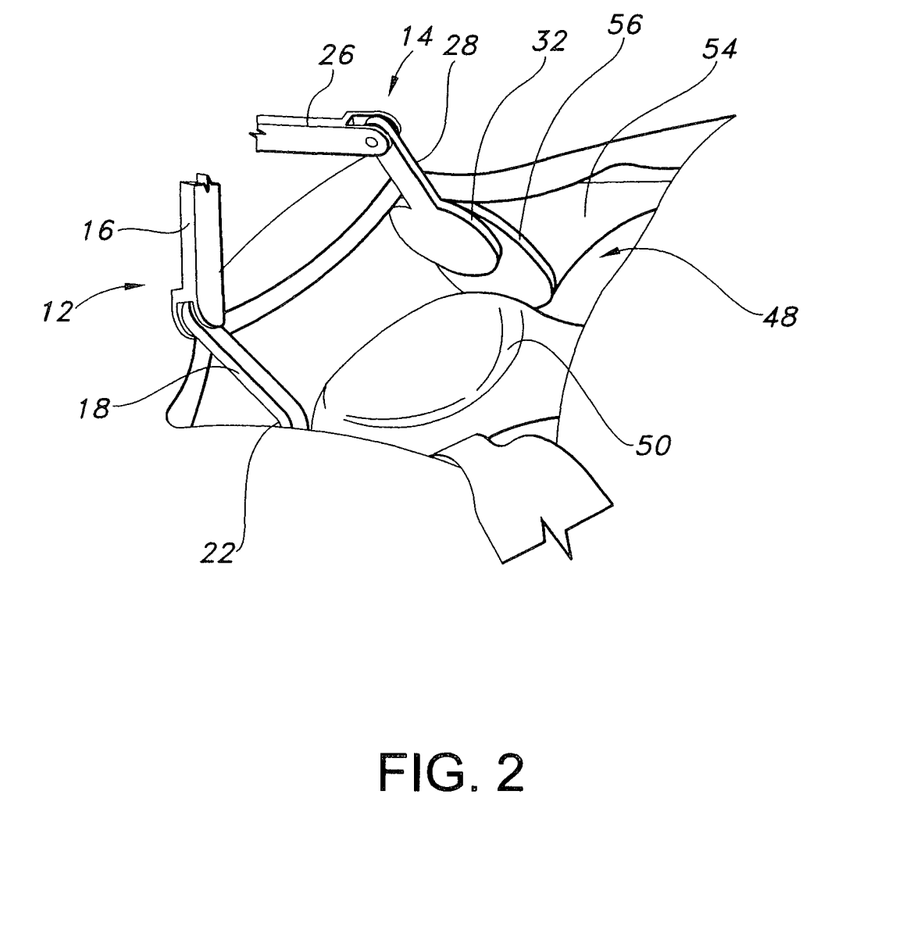
FIG. 2 is a perspective view of the retractor of FIG. 1 shown in an orthopaedic surgery.

The second portion 28 is coupled to a second retaining member 32. The second retaining member 32 is sized and shaped to abut a resected humerus 54 (shown in FIG. 2). In the illustrated embodiment, the second retaining member 32 is a disk 34. The flat side of the disk 34 abuts and presses against the resected humerus (FIG. 2). Also, in the illustrated embodiment, the retaining member 32 and the second portion 28 are integral with one another. However, in other embodiments, the retaining member 32 may be a separate part from the second portion 28. In such embodiments, the retaining member 32 may be fixedly coupled to the second portion 28 or the retaining member 32 may be movably coupled to the second portion 28. In some embodiments, the retaining member 32 may be pivotally coupled to the second portion 28. In the embodiment where the retaining member 32 is not integral with the second portion 28, any known connection method may be used (whether fixedly connecting or movably connecting).

Because both the second portion 18 of the first arm 12 and the second portion 28 of the second arm 14 are hinged, the second portions 18, 28 can be completely rotated about the first portions 16, 26. The angles α and θ can range anywhere from zero (or nearly zero) degrees to 360 (or nearly three hundred sixty) degrees. In other words, the second portions 18, 28 of the first and second arms 12, 14 can be rotated almost all the way around the first portions 16, 26. This is useful because it allows for the angles α and θ to be adjusted to allow for placement in any location. Also, and especially important, is that the hinges 20, 30 allow the second portions 18, 28 to be rotated so that the angles α and θ are approximately 270 degrees. This effectively flips the retractor 10, so that it can be used on either shoulder. For example, when the second portions 18, 28 are at 90 degrees from the first portions 16, 26, the retractor 10 is adapted to be used on the patient's left shoulder. However, using the hinges 20, 30, the second portions 18, 28 can be swung around to an angle of approximately 270 degrees and the retractor 10 can be used on a patient's right shoulder. This decreases the number of instruments that need to be in an instrument set and also lowers the cost, since only one instrument needs to be made.

Referring back now to the first portions 16, 26 of the first and second arms 12, 14, the first portions 16, 26 include handles 36, 38, respectively. The handles 36, 38 allow the user to grip the retractor 10. The first portions 16, 26 of the first and second arms 12, 14 are coupled together with a pivot pin 40. The pivot pin 40 allows the first and second arms 12, 14 to pivot relative to one another. The two first portions 16, 26 are also linked together via a linking mechanism 42. In this embodiment, the linking mechanism 42 is located at the distal end and includes ratchets 44. The end of the first arm 12 engages the space between the ratchets 44, locking the first portion 16 of the first arm 12 in place relative to the first portion 26 of the second arm 14. In other embodiments, the second arm 14 may engage the ratchets 44 or both arms 12, 14 may engage the ratchets. Also included between the first portions 16, 26 of the first and second arms 12, 14 is a biasing member 46. In this embodiment, the biasing member 46 is a steel spring that provides the resistance necessary between the two arms 12, 14 to engage the ratchets 44 and hold the arms 12, 14 in place. The tension created by the biasing member 46 allows the user to let go of the retractor 10 and still have the retractor stay in place—freeing up the user's hands to perform other aspects of the surgery.

Figure 3:
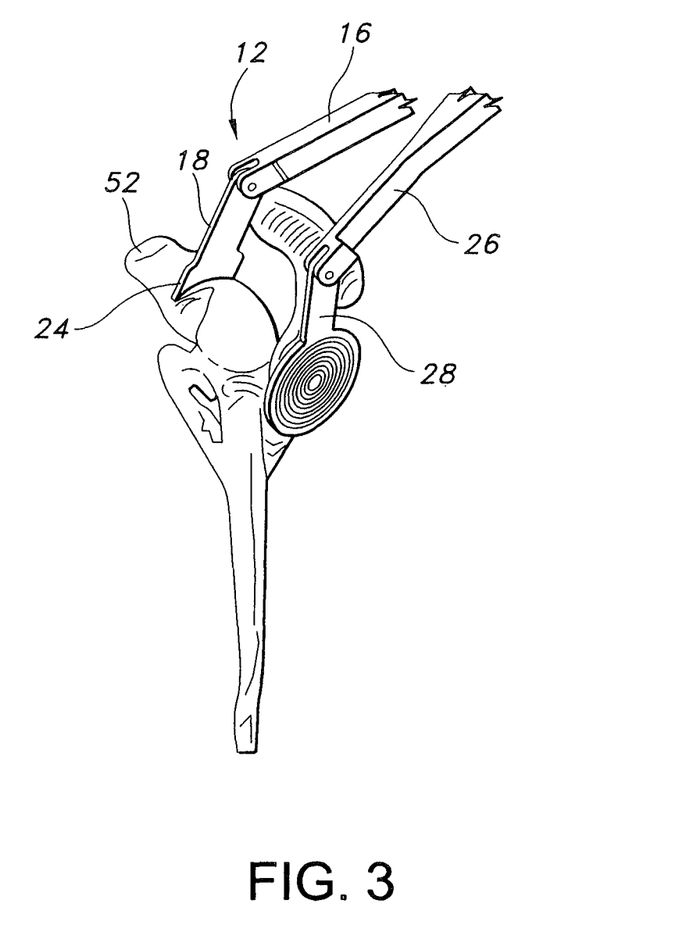
FIG. 3 is a view of the retractor of FIG. 1 engaging the coracoid process.

Turning now to FIG. 2, the retractor 10 is illustrated during use. As shown, the retractor 10 is placed into the surgical opening 48. The second portions 18, 28 of the first and second arms 12, 14 press against skin and tissue in order to keep the surgical opening 48 open so as to reveal a patient's glenoid 50. As illustrated in FIG. 3, the second portion 18 of the first arm 12 engages the coracoid process 52. As shown in FIG. 3, the u-shaped member 24 grasps the coracoid process 52. Returning now to FIG. 2, the second portion 28 of the second arm 14 couples to a resected humerus 54 by abutting a bone cover 56 that has been placed on the resected humerus 54. In other embodiments, the second portion 28 may abut the resected humerus 54 directly.

As is illustrated in FIG. 2, the first portions 16, 26 hang over the side of the retracted skin and tissue. Also, as shown, by having the first arm 12 of the retractor couple to the coracoid process, a greater portion of the glenoid is revealed than in previous designs. Also, since the retractor 10 does not abut the glenoid, more of the glenoid is exposed than in prior art designs.

Figure 4:
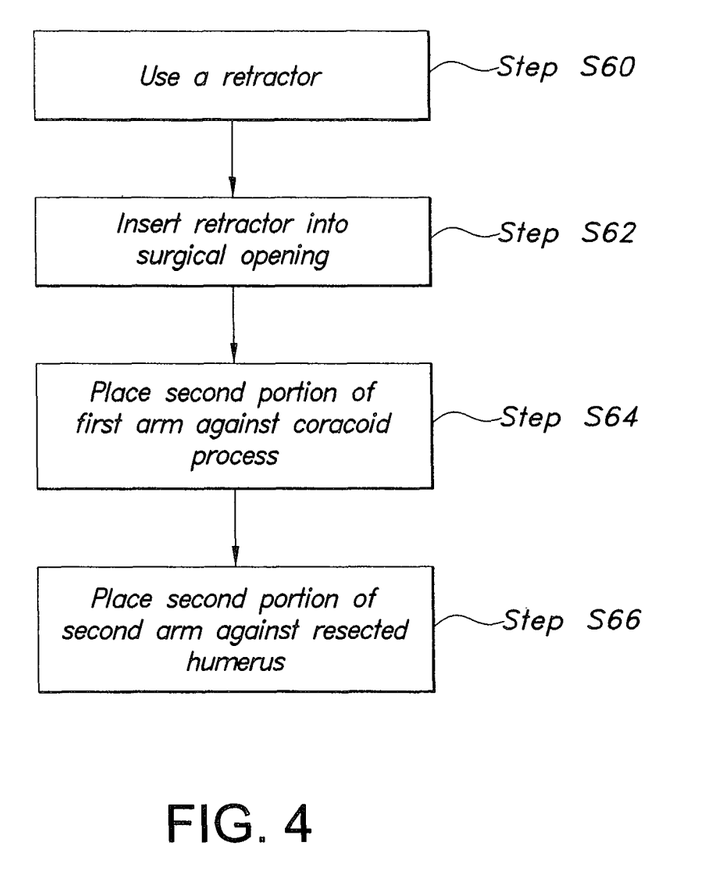
FIG. 4 is a flow chart illustrating a method according to one embodiment of the present invention.

Turning now to FIG. 4, a method for using the retractor 10 according to one embodiment of the present invention will be described. At step s60, the retractor 10 is used. The retractor 10 includes the first arm 12 and the second arm 14. The first arm 12 has the first portion 16 and the second portion 18. The second arm 14 also includes the first portion 26 and the second portion 28. At step s62, the retractor is inserted into the surgical opening 48. The second portion 18 of the first arm 12 is placed against the coracoid process 52 at step s64. In the present embodiment, the second portion 18 of the first arm 12 is placed at the base of the coracoid process 52. In other embodiments, the second portion 18 of the first arm 12 may be placed against other portions of the coracoid process 52. The second portion 28 of the second arm 14 is placed against the resected humerus 54 at step s66. This includes having the second portion 28 abut a surgical cover 56. The first portions 16, 26 of the first and second arms 12, 14 may then be placed outside the incision space.

Figure 5:
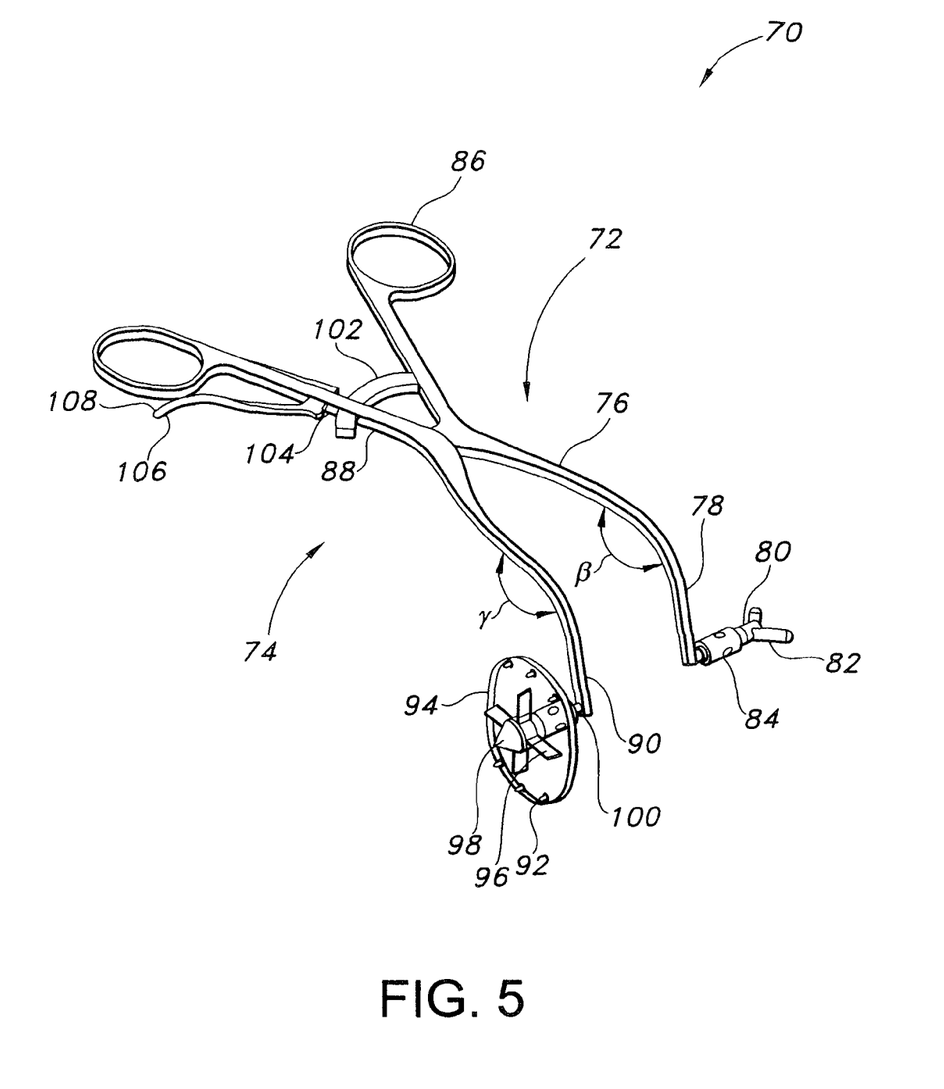
FIG. 5 is a perspective view of a retractor according to another embodiment of the present invention.

Turning now to FIG. 5, a retractor 70 according to another embodiment of the present invention is illustrated. As shown, the retractor 70 includes a first arm 72 and a second arm 74. The first arm 72 includes a first portion 76 and a second portion 78. The second portion 78 is bent relative to the first portion 76 at an angle β.

The second portion 78 includes a first retaining member 80. The first retaining member 80 is sized and shaped to abut and press against the coracoid process. In this embodiment, the first retaining member 80 is a clawed foot 82. The clawed foot 82 is pivotally coupled to the second portion 78 via a pivot pin 84. The pivot pin 84 allows the clawed foot 82 to rotate about the second portion 78 in order to optimize the hold on the coracoid process. In other embodiments in which the clawed foot 82 is a separate piece from the second portion 78, other known attachments may be used. In yet other embodiments, the clawed foot 82 may be integral with the second portion 78. Alternatively, the clawed foot 82 may be a separate piece from the second portion 78, but may be fixedly attached to the second portion 78. In other embodiments in which the clawed foot 82 is a separate piece from the second portion 78, other known attachments may be used.

Turning now to the second arm 74, the second arm 74 includes a first portion 88 and a second portion 90. The second portion 90 is bent relative to the first portion 88 at an angle γ. The second portion 90 includes a second retaining member 92. The second retaining member 92 is sized and shaped to abut and press against the resected humerus 54. In this embodiment, the second retaining member 92 is a disk 94. The disk 94 includes a cruciform 96 having a spike 98. The spike 98 engages the resected head of the humerus. In this embodiment, the hole made by the spike 98 is not any larger than a hole made by the stem that will eventually be inserted into the resected humerus. In other embodiments, the second retaining member 92 abuts a protective cover (such as the one shown in FIG. 2) on the resected head and the cruciform 96 and spike 98 are inserted into a corresponding recess (or recesses) in the cover. In yet other embodiments, the spike 98 engages an opening in a broach that is inserted into the humerus. In such embodiments, the user would broach the humerus as is known in the art and then leave the broach inserted while preparing the glenoid. The user would then insert the spike into the corresponding opening in the broach, such that the second retaining member 92 engages the broach and positioning the second retaining member 92 against the humerus. In some embodiments, the spike 98 might lock into an opening in the broach. In other embodiments, the spike 98 may not be in locked engagement, but instead may only engage the broach.

The disk 94 is pivotally coupled to the second portion 90 via a pivot pin 100. The pivot pin 100 allows the disk 94 to rotate about the second portion 90 in order to best fit on the resected humerus. In other embodiments in which the disk 94 is a separate piece from the second portion 90, other known attachments may be used. In yet other embodiments, the disk 94 may be integral with the second portion 90. Alternatively, the disk 94 may be a separate piece from the second portion 90, but may be fixedly attached to the second portion 90. In other embodiments in which the disk 94 is a separate piece from the second portion 90, other known attachments may be used.

Turning now to the first portions 76, 88 of the first and second arms 72, 74, the first portions 76, 88 are coupled via a linking mechanism 102. In this embodiment, the linking mechanism 102 is a ratchet mechanism that extends from the first portion 76 of the first arm 72. The first portion 88 of the second arm 74 includes a recess (104) for engaging the linking mechanism 102. A locking mechanism 106 engages the linking mechanism 102 to lock it into place. The locking mechanism 106 includes a handle 108 that can be easily engaged by the user to release the linking mechanism 102.

Figure 6:
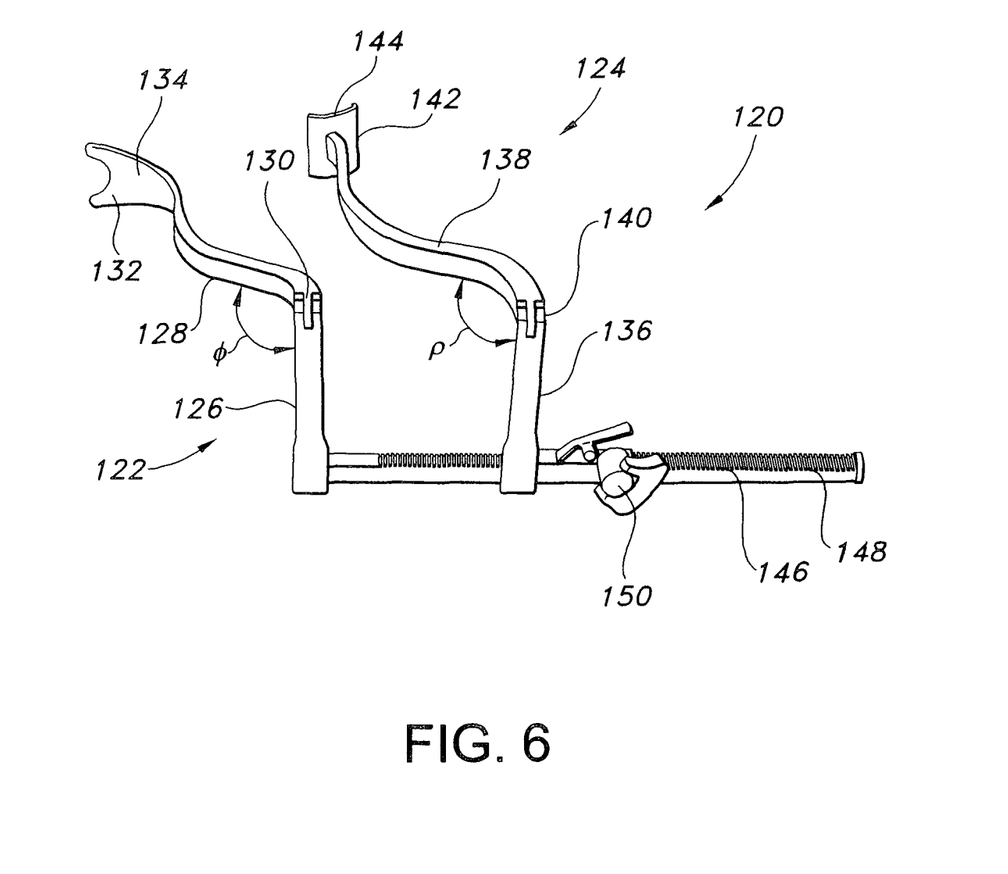
FIG. 6 is a perspective view of a retractor according to yet another embodiment of the present invention.

Turning now to FIG. 6, another embodiment of the present invention is illustrated. In this embodiment, a retractor 120 is shown. The retractor 120 includes a first arm 122 and a second arm 124. The first arm 122 has a first portion 126 and a second portion 128. The second portion 128 is movably coupled to the first portion 126. In this embodiment, the first portion 126 and the second portion 128 are coupled via a hinge 130. However, in other embodiments, other coupling mechanisms that allow the second portion 128 to move relative to the first portion 126 may be used. The hinge 130 allows the second portion 128 to be set at an angle φ relative to the first portion 126.

The second portion 128 is coupled to a first retaining member 132. The retaining member 132 is sized and shaped to retain a portion of a coracoid process (shown in FIG. 2). In the illustrated embodiment, the retaining member 132 is a u-shaped member 134 that is designed to press against the coracoid process. Also, in the illustrated embodiment, the retaining member 132 and the second portion 128 are integral with one another. However, in other embodiments, the retaining member 132 may be a separate part from the second portion 128. In such embodiments, the retaining member 132 may be fixedly coupled to the second portion 128 or the retaining member 132 may be movably coupled to the second portion 128. In some embodiments, the retaining member 132 may be pivotally coupled to the second portion 128. In the embodiment where the first retaining member is not integral with the second portion 128, any known connection method may be used (whether fixedly connecting or movably connecting).

The second arm 124 of the spreadable retractor 120 is movably coupled to the first arm 122. The second arm 124 includes a first portion 136 and a second portion 138 that is movably coupled to the first portion 136. In the illustrated embodiment, the first portion 136 is coupled to the second portion 138 via a hinge 140. However, in other embodiments, other coupling mechanisms that allow the second portion 138 to move relative to the first portion 136 may be used. The hinge 140 allows the second portion 138 to be set at an angle ρ relative to the first portion 136.

The second portion 138 is coupled to a second retaining member 142. The second retaining member 142 is sized and shaped to abut a resected humerus (shown in FIG. 2). In the illustrated embodiment, the second retaining member 142 is a curved piece 144. The curved outside of the curved piece 144 abuts and presses against the humeral shaft below the head. Also, in the illustrated embodiment, the retaining member 142 and the second portion 138 are integral with one another. However, in other embodiments, the retaining member 142 may be a separate part from the second portion 138. In such embodiments, the retaining member 142 may be fixedly coupled to the second portion 138 or the retaining member 142 may be movably coupled to the second portion 138. In some embodiments, the retaining member 142 may be pivotally coupled to the second portion 138. In the embodiment where the first retaining member 142 is not integral with the second portion 138, any known connection method may be used (whether fixedly connecting or movably connecting).

Because both the second portion 128 of the first arm 122 and the second portion 138 of the second arm 124 are hinged, the second portions 128, 138 can be completely rotated about the first portions 126, 136. The angles φ and ρ can range anywhere from zero (or nearly zero) degrees to 360 (or nearly three hundred sixty) degrees. In other words, the second portions 128, 138 of the first and second arms 122, 124 can be rotated almost all the way around the first portions 126, 136. This is useful because it allows for the angles φ and ρ to be adjusted to allow for placement in any location. Also, and especially important, is that the hinges 130, 140 allow the second portions 128, 138 to be rotated so that the angles φ and ρ are approximately 270 degrees. This effectively flips the retractor 120, so that it can be used on either shoulder. For example, when the second portions 128, 138 are at 90 degrees from the first portions 126, 136, the retractor 120 is adapted to be used on the patient's left shoulder. However, using the hinges 130, 140, the second portions 128, 138 can be swung around to an angle of approximately 270 degrees and the retractor 120 can be used on a patient's right shoulder. This decreases the number of instruments that need to be in an instrument set and also lowers the cost, since only one instrument needs to be made.

Referring back now to the first portions 126, 136 of the first and second arms 122, 124, the first portions 126, 136 include a linking mechanism 146. In this embodiment, the linking mechanism 146 is located at the distal end and includes ratchets 148. The ends of both the first arm 122 and second arm 124 engage the space between the ratchets 148, locking the first portion 126 of the first arm 122 in place relative to the first portion 136 of the second arm 124. In other embodiments, the second arm 124 may engage the ratchets 148 or both arms 122, 124 may engage the ratchets. A locking feature 150 is included on the linking mechanism 146 to lock the arms 122, 124 in position relative to one another.

While the invention is susceptible to various modifications and alternative forms, a specific embodiment thereof has been shown by way of example in the drawings and will herein be described in detail. It should be understood, however, that there is no intent to limit the invention to the particular form disclosed, but on the contrary, the intention is to cover all modifications, equivalents, and alternatives falling within the spirit and scope of the invention as defined by the appended claims.

The invention claimed is:

1. A spreadable retractor for use in joint arthroplasty comprising:
 a first arm having a first portion and a second portion, the second portion being hingedly coupled to the first portion, the second portion comprising a plate-like member having a u-shaped element adapted to receive a coracoid process; and
 a second arm movably coupled to the first arm, the second arm having a first portion and a second portion, the second portion being hingedly coupled to the first portion, the second portion comprising a plate-like member having a disc adapted to abut a resected humerus.

2. The spreadable retractor of claim 1, wherein the first and second arm are coupled to one another via a linking mechanism.

3. The spreadable retractor of claim 2, wherein the linking mechanism includes a ratchet.

4. The spreadable retractor of claim 2, further including a locking mechanism, the locking mechanism coupled to the linking mechanism and sized and shaped to lock the linking mechanism in a particular position.

5. A spreadable retractor for use in joint arthroplasty comprising:
 a first arm having a first portion and a second portion, the second portion being hingedly coupled to the first portion, the second portion comprising a plate-like member having a u-shaped element adapted to receive a coracoid process; and
 a second arm movably coupled to the first arm, the second arm having a first portion and a second portion, the second portion being hingedly coupled to the first portion, the second portion comprising a plate-like member having a disc adapted to abut a resected humerus.

* * * * *